United States Patent
Iddan et al.

(10) Patent No.: US 8,394,034 B2
(45) Date of Patent: Mar. 12, 2013

(54) DEVICE, SYSTEM AND METHOD FOR IN-VIVO SAMPLING

(75) Inventors: Gavriel J. Iddan, Haifa (IL); Elisha Rabinovitz, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 11/597,103

(22) PCT Filed: May 22, 2005

(86) PCT No.: PCT/IL2005/000524
§ 371 (c)(1),
(2), (4) Date: Nov. 19, 2007

(87) PCT Pub. No.: WO2005/113374
PCT Pub. Date: Dec. 1, 2005

(65) Prior Publication Data
US 2008/0208077 A1    Aug. 28, 2008

Related U.S. Application Data

(60) Provisional application No. 60/572,775, filed on May 21, 2004, provisional application No. 60/573,377, filed on May 24, 2004.

(51) Int. Cl.
*A61F 2/02* (2006.01)
*A61B 5/00* (2006.01)
*B65D 81/00* (2006.01)

(52) U.S. Cl. ........ 600/582; 600/101; 600/573; 600/575; 600/584; 604/317; 604/323

(58) Field of Classification Search .......... 600/101, 600/103, 109–110, 309–310, 314, 350, 352, 600/573, 575, 579, 582, 584; 604/317, 323
See application file for complete search history.

(56) References Cited

U.S. PATENT DOCUMENTS

| | | | | |
|---|---|---|---|---|
| 3,750,476 A | * | 8/1973 | Brown | 73/724 |
| 4,278,077 A | | 7/1981 | Mizumoto | |
| 4,481,952 A | * | 11/1984 | Pawelec | 600/582 |
| 5,167,626 A | | 12/1992 | Casper et al. | |
| 5,318,557 A | | 6/1994 | Gross | |
| 5,395,366 A | | 3/1995 | D'Andrea et al. | |
| 5,604,531 A | | 2/1997 | Iddan et al. | |
| 5,674,530 A | | 10/1997 | Amidon et al. | |
| 5,901,939 A | * | 5/1999 | Cabuz et al. | 251/129.02 |
| 5,993,378 A | | 11/1999 | Lemelson | |
| 6,007,309 A | * | 12/1999 | Hartley | 417/322 |

(Continued)

FOREIGN PATENT DOCUMENTS

| | | |
|---|---|---|
| DE | 344 0177 | 11/1984 |
| EP | 0 061 783 | 10/1982 |

(Continued)

OTHER PUBLICATIONS

International Search Report for International Application No. PCT/IL05/00524 filed May 22, 2005, issued Feb. 20, 2007.

(Continued)

*Primary Examiner* — Rene Towa
(74) *Attorney, Agent, or Firm* — Pearl Cohen Zedek Latzer, LLP

(57) ABSTRACT

A device, system and method for in-vivo sampling. An in-vivo device and method for use thereof may include a sampling chamber and a gating mechanism. The sampling chamber may store a sample of a body lumen substance, and the gate may close and open an opening of the sampling chamber.

23 Claims, 8 Drawing Sheets

U.S. PATENT DOCUMENTS

| | | | |
|---|---|---|---|
| 6,168,395 B1* | 1/2001 | Quenzer et al. | 417/413.3 |
| 6,240,312 B1 | 5/2001 | Alfano et al. | |
| 6,558,528 B1* | 5/2003 | Matzinger | 205/777.5 |
| 6,868,739 B1* | 3/2005 | Krivitski et al. | 73/861.05 |
| 6,929,636 B1 | 8/2005 | Von Alten | |
| 7,578,788 B2 | 8/2009 | Yokoi et al. | |
| 2001/0017649 A1* | 8/2001 | Yaron | 348/45 |
| 2002/0103417 A1 | 8/2002 | Gazdzinski | |
| 2002/0111544 A1* | 8/2002 | Iddan | 600/310 |
| 2002/0131230 A1* | 9/2002 | Potter | 361/277 |
| 2002/0132226 A1* | 9/2002 | Nair et al. | 435/4 |
| 2002/0198470 A1 | 12/2002 | Imran et al. | |
| 2003/0181788 A1 | 9/2003 | Yokoi et al. | |
| 2003/0212346 A1 | 11/2003 | Yuzhakov et al. | |
| 2004/0023236 A1* | 2/2004 | Potter et al. | 435/6 |
| 2004/0053268 A1* | 3/2004 | Karlsen | 435/6 |
| 2004/0115877 A1* | 6/2004 | Iddan | 438/200 |
| 2004/0122315 A1 | 6/2004 | Krill | |
| 2004/0143236 A1* | 7/2004 | Santini et al. | 604/500 |
| 2004/0209354 A1* | 10/2004 | Mathies et al. | 435/287.2 |
| 2005/0031688 A1* | 2/2005 | Ayala | 424/473 |

FOREIGN PATENT DOCUMENTS

| | | |
|---|---|---|
| EP | 0061783 | 10/1982 |
| EP | 0 662 304 | 7/1995 |
| JP | 57-163309 | 10/1982 |
| JP | 1992-144533 | 5/1992 |
| JP | 2003-523795 | 8/2003 |
| JP | 2003-275170 | 9/2003 |
| WO | WO 01/35813 | 5/2001 |

OTHER PUBLICATIONS

Supplementary European Search Report for Application No. 05741998 filed Nov. 20, 2006, issued Dec. 21, 2007.

* cited by examiner

DEVICE, SYSTEM AND METHOD FOR IN-VIVO SAMPLING

CROSS-REFERENCE TO RELATED APPLICATIONS

This application is a national phase application of PCT International Application No. PCT/IL2005/000524, International Filing Date 22 May 2005, claiming priority of US Provisional Application No. 60/572,775 filed 21 May 2004 and of US Provisional Application No. 60/573,377 filed 24 May 2004, each of which is hereby incorporated by reference in its entirety.

FIELD OF THE INVENTION

The present invention relates in general to in-vivo testing and/or therapy.

BACKGROUND OF THE INVENTION

An atypical concentration or presence of substances in body fluids or in body lumens may be indicative of the biological condition of the body. For example, the presence of elevated concentrations of red blood cells in the gastrointestinal (GI) tract may indicate different pathologies, depending on the location of the bleeding along the GI tract. Thus, for example, bleeding in the stomach may indicate an ulcer, whereas bleeding in the small intestine may indicate the presence of a tumor. Furthermore, different organs may contain different body fluids requiring different analysis methods. For example, the stomach secretes acids whereas pancreatic juice is basic.

Medical detection kits are usually based on in vitro testing of body fluid samples for the presence of a suspected substance. For example, in some cases, diseases, such as cancer, are detected by analyzing the blood stream for tumor specific markers, typically, specific antibodies. A drawback of this method is that the appearance of antibodies in the blood stream usually occurs at a late stage of the disease, such that early detection is not possible using this method. Furthermore, this method of detection does not easily allow localization or identification of the origin of a pathology.

Early detection, identification and location of abnormal conditions (such as, for example, an atypical presence or concentration of a substance) may be critical for definitive diagnosis and/or treating of various pathologies.

Devices, systems and methods for in-vivo sensing of passages or cavities within a body, and for sensing and gathering information (e.g., image information, pH information, temperature information, electrical impedance information, pressure information, etc.), are known in the art.

An in-vivo sensing system may include, for example, an in-vivo imaging device for obtaining images from inside a body cavity or lumen, such as the GI tract. The in-vivo imaging device may include, for example, an imager associated with units such as, for example, an optical system, an illumination source, a controller, a power source, a transmitter, and an antenna. The in-vivo imaging device may transmit acquired image data to an external receiver/recorder, using a communication channel (e.g., Radio Frequency signals). Other types of in-vivo devices exist, such as endoscopes which may not require a transmitter, and in-vivo devices performing functions other than imaging.

SUMMARY OF THE INVENTION

Various embodiments of the invention provide, for example, a gating mechanism for an in-vivo device.

Some embodiments of the present invention, for example, may include a gating mechanism for an in-vivo device that allows activating or initiating a certain procedure, for example, enabling a testing sample to enter a testing chamber, or enabling the release of certain substances (such as medicaments), only under specified conditions such as time, location, environmental conditions, etc.

According to some embodiments, a gating mechanism may enable differential activation of an in-vivo device under specified conditions such as time, location, environmental conditions, etc.

In some embodiments, for example, the in-vivo device may include a sampling chamber able to store a sample of a body lumen substance, and a gate able to close and open an opening of the sampling chamber. In one embodiment, the gate may be a passive gate, for example, an autonomous gate, a non-controllable gate, a non-controlled gate, a gate which may be able to open and/or close after the device in inserted into a body, a gate which opening and/or closing is not controlled or commanded after the device is inserted in to a body, or the like. In another embodiment, the gate may be an active gate, for example, a controlled gate, a controllable gate, a non-autonomous gate, a gate which opening and/or closing may be controlled or triggered by a user or an external device or system, a gate which operation utilizes an active opening or closing mechanism (e.g., mechanical mechanism, electronic or electrical mechanism, magnetic mechanism, etc.), or the like.

In some embodiments, for example, the in-vivo device may include a controller able to open the gate when a pre-defined condition is met, and/or in response to a signal. The signal may be received from an external transmitter, may be generated based on an analysis of an in-vivo image, or may be generated by an in-vivo sensor in response to a sensed parameter, e.g., temperature, pH, pressure, enzyme activity, or the like. Other suitable methods of controlling, opening and/or closing the gate may be used.

In some embodiments, for example, the in-vivo device may include an absorbent component to absorb at least a portion of the body lumen substance.

In some embodiments, for example, the in-vivo device may include a vacuumized compartment.

In some embodiments, for example, the in-vivo device may include a capillary inlet to transport the body lumen substance into the chamber, or a wide inlet to freely transport the body lumen substance into the chamber.

In some embodiments, for example, the in-vivo device may include a pump to pump-in the body lumen substance into the chamber, or to pump-out a content from the chamber.

In some embodiments, for example, the in-vivo device may include a sampling chamber having a reagent or an indicator to interact with the sampled body lumen substance.

In some embodiments, for example, the in-vivo device may include a first, flexible conductive plate able to repel from a second conductive plate when current is supplied to the first and second conductive plates; and a power source to supply current to the first and second conductive plates.

In some embodiments, for example, the in-vivo device may include a well having a cavity between the first and second conductive plates.

In some embodiments, for example, the in-vivo device may include a first well having a first cavity between the first and second conductive plates, and a second well having a second cavity between the first and second conductive plates.

In some embodiments, for example, the sample may be able to advance from the first well to the second well, or from a first sampling chamber to a second sampling chamber.

In some embodiments, for example, the first well (or a first sampling chamber) may include a first reagent or indicator, and a second well (or a second sampling chamber) may include a second, different reagent or indicator.

In some embodiments, for example, the gate may include a dissolvable material.

In some embodiments, for example, the in-vivo device may include an imager to acquire an image of the chamber.

In some embodiments, for example, the in-vivo device may include a first chamber to collect a first body lumen substance, and a second chamber to collect a second body lumen substance.

In some embodiments, for example, the in-vivo device may include a first gate to close an opening of the first chamber, and a second gate to close an opening of the second chamber.

In some embodiments, for example, the first gate may be substantially open when the second gate is substantially closed.

In some embodiments, for example, at least one of the first and second gates may be dissolvable.

In some embodiments, for example, the second gate is able to substantially completely dissolve after the first gate is able to substantially completely dissolve.

In some embodiments, for example, the first gate may include a first volume of a dissolvable material, and the second gate may include a second, different volume of the dissolvable material.

In some embodiments, for example, the first gate may include a first dissolvable material, and the second gate may include a second, different dissolvable material.

In some embodiments, for example, the first material is dissolvable in response to a first pH level, and the second material is dissolvable in response to a second, different pH level.

In some embodiments, for example, the first material is dissolvable in response to a first temperature, and the second material is dissolvable in response to a second, different temperature.

In some embodiments, for example, the first material is dissolvable in response to a first pressure, and the second material is dissolvable in response to a second, different pressure.

In some embodiments, for example, the first material is dissolvable in response to a first enzymatic activity, and the second material is dissolvable in response to a second, different enzymatic activity.

Some embodiments may include, for example, an in-vivo imaging device which may be autonomous and/or may include a swallowable capsule.

Some embodiments of the invention may include a method for in-vivo sampling, which may include, for example: collecting a substance in a sampling chamber of an in-vivo device, wherein the sampling chamber has an opening closeable by a gate; acquiring (e.g., in-vivo) an image of the sampling chamber; opening the gate at a point in time after insertion of the in-vivo device into a body; and/or other suitable operations.

Some embodiments of the present invention, for example, may allow particular timing and/or localization of operations of an in-vivo device. For example, according to an embodiment of the invention, a method for in-vivo analysis may include coordinating an in-vivo sampling process at a specific location along the GI tract, for example, at the duodenum, where typically high concentrations of pancreatic cancer or other pancreatic pathologies may be found.

Embodiments of the invention may allow various other benefits, and may be used in conjunction with various other applications.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
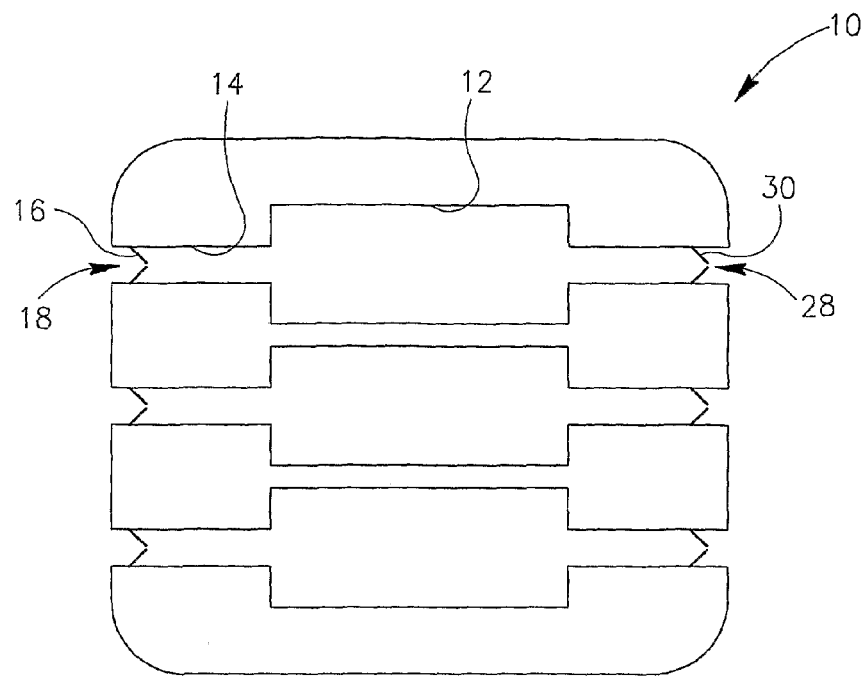
FIG. 1 is a schematic illustration, along the transverse plane, of an in-vivo device, constructed and operative in accordance with an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

It should be noted that although a portion of the discussion may relate to in-vivo imaging devices, systems, and methods, the present invention is not limited in this regard, and embodiments of the present invention may be used in conjunction with various other in-vivo sensing devices, systems, and methods. Embodiments of the invention are typically autonomous, and are typically self-contained. For example, a device may be a capsule or other unit where all the components are substantially contained within a container or shell or housing, and/or where the device does not require any wires or cables to, for example, receive power or transmit information. For example, some embodiments of the invention may be used, for example, in conjunction with autonomous in-vivo sensing of pH, in-vivo sensing of temperature, in-vivo sensing of pressure, in-vivo sensing of electrical impedance, in-vivo detection of a substance or a material, in-vivo detection of a medical condition or a pathology, in-vivo acquisition or analysis of data or images, in-vivo imaging, in-vivo light or color detection or analysis, and/or various other in-vivo sensing devices, systems, and methods. Some embodiments of the invention may be used not necessarily in the context of in-vivo imaging or in-vivo sensing.

Some embodiments of the present invention are directed to a typically swallowable in-vivo sensing device, e.g., a typically swallowable in-vivo imaging device. Devices according to embodiments of the present invention may be similar to, or may include elements or component similar to, embodiments described in U.S. patent application Ser. No. 09/800,470, entitled "Device And System For In-vivo Imaging", filed on 8 Mar., 2001, published on Nov. 1, 2001 as United States Patent Application Publication Number 2001/0035902, and/or in U.S. Pat. No. 5,604,531 to Iddan et al., entitled "In-vivo Video Camera System", each of which is assigned to the common assignee of the present invention and each of which is hereby fully incorporated by reference. Furthermore, a receiving and/or display system which may be suitable for use with embodiments of the present invention may also be similar to embodiments described in U.S. patent application Ser. No. 09/800,470 and/or in U.S. Pat. No. 5,604,531. Devices and systems as described herein may have other configurations and/or other sets of components. For example, the present invention may be practiced using an endoscope, needle, stent, catheter, etc.

Some embodiments of the invention may provide a gating mechanism for an in-vivo device that allows activating or initiating a certain procedure, such as, for example, enabling a testing sample to enter a testing chamber, e.g., only under specified conditions such as, for example, time, location, environmental conditions, etc.

According to some embodiments of the invention, a gating mechanism may enable the release of certain substances (such as medicaments, stains, markers, or the like) under specified conditions such, for example, as time, location, environmental conditions, etc.

According to some embodiments, a gating mechanism may enable differential activation of an in-vivo device under specified conditions such as, for example, time, location, environmental conditions, etc.

According to an embodiment of the present invention, there may be multiple chambers, some of which may be gated, for example, in order to allow testing samples to be drawn into the testing chambers at specified times or locations within a body lumen; others may release or pump out or inject substances, such as medicaments, under such conditions. This may allow for more precise knowledge of the location from which a sample was taken and/or enable more precise administering of a substance.

Figure 2:
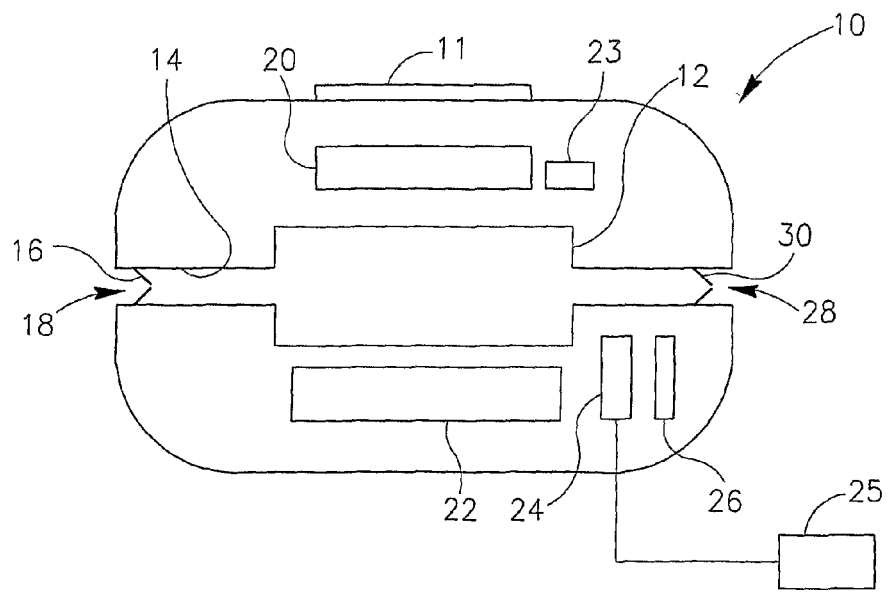
FIG. 2 is a schematic illustration of the device of FIG. 1, seen along the lateral plane.

Reference is now made to FIGS. 1 and 2, which depict an in-vivo device 10, such as swallowable device, which may be for example a capsule and/or autonomous swallowable capsule, but which may have other forms, according to an embodiment of the invention. FIG. 1 depicts a transverse plane illustration of the device 10, and FIG. 2 depicts a lateral plane illustration of the device 10, both showing longitudinal sections substantially at a right angle to each other.

Device 10 may include, for example, multiple sampling chambers 12. Device 10 may be inserted into a human body, e.g., by swallowing device 10. Bodily fluid samples may enter sampling chamber 12 through an inlet 14, whose opening 18 may be closed off by a gate 16. There may be an outlet 28, which may have a valve 30 to control the outflow of fluid samples.

Optionally, device 10 may further include an illuminator 20 to illuminate sampling chamber 12; a detector 22 to detect the samples or a reaction that may occur between components of a sample and indicators possibly contained within chamber 12; a transmitter 24 to transmit the output of detector 22; and a power source 26 to power the electronic elements of device 10. Transmitter 24 may be a wireless transmitter, for example, able to transmit Radio Frequency (RF) signals. In some embodiments, sampling chamber 12 may be transparent or semi-transparent, such that its contents may be viewed and/or imaged by detector 22.

Detector 22 may include a photodetector or it may include an image sensor, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, bodily fluids may enter opening 18 of inlet 14 through gate 16. If gate 16 allows the fluid to enter, the fluid may travel through chamber 12 and may then flow out of outlet 28.

In some embodiments, the in-vivo device 10 may optionally include one or more sensing means, e.g., to obtain physiological or other information of the body lumen being sampled. For example, the device 10 may include a sensor 23 or multiple sensors which may include, for example a pH sensor, a temperature sensor, a pressure sensor, a sensor of electrical impedance, an ultrasound detector, a radiation detector, or the like.

In some embodiments, device 10 may optionally include an image sensor for imaging the body lumen and/or for obtaining images of the sampling chamber(s). The device 10 may include a transparent section, such as window 11, through which the body lumen may be illuminated and imaged by an image sensor (such as sensor 23 or a detector similar to detector 22). Illuminator 20 and/or other dedicated illumination sources may be used to illuminate the body lumen. Optionally, device 10 may include an optical system having elements such as lenses, mirrors, collimators, etc. may be used with an image sensor. Image data or other data collected by sensor 23 may be transmitted, typically wirelessly, to an external receiving unit 25.

Embodiments of the in-vivo device 10 may typically be autonomous and may typically be self-contained.

Figure 3:
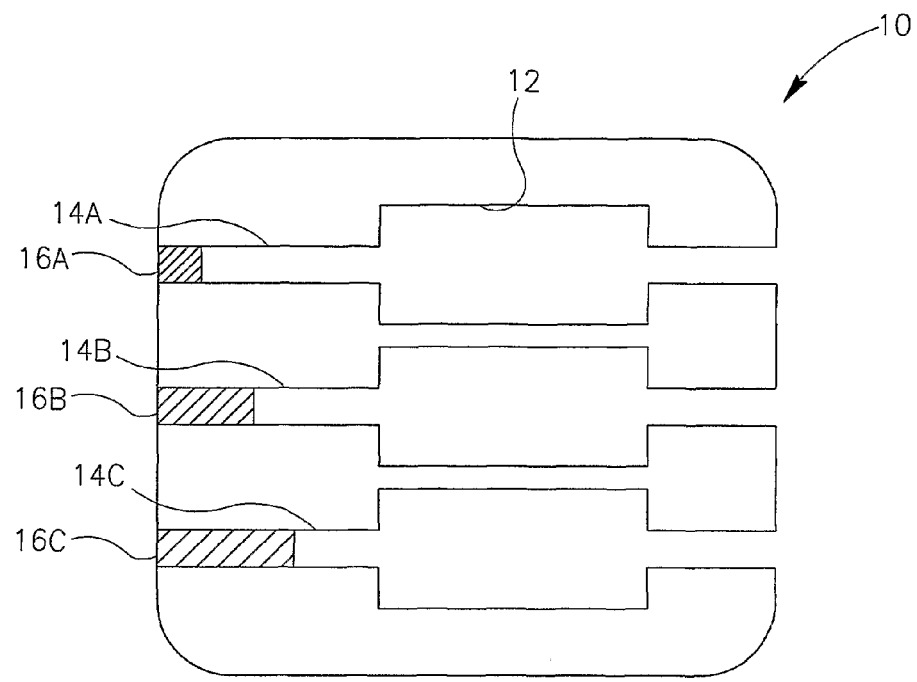
FIGS. 3, 4 and 5 are schematic illustrations of gating mechanisms, according to embodiments of the invention.

Reference is now made to FIG. 3, which depicts an embodiment of device 10 having multiple gates 16. In this embodiment, gates 16A, 16B and 16C may be made of, for example, a dissolvable material that may dissolve over time.

According to some embodiments, the dissolving may be differential, wherein for example, gate 16A may be made of a dissolvable material of one volume, gate 16B may be made of a dissolvable material of a greater volume than gate 16A, and gate 16C may be made of a greater volume of dissolvable material than gate 16B.

Additionally or alternatively, different materials, having different properties which may affect their dissolving rates, may be used in the different gates 16. According to some embodiments, a combination of materials may be used to achieve differential dissolving of gates 16.

Some dissolvable materials according to embodiments of the invention may include biocompatible degradable materials, for example, polymers such as polyethylene glycol, natural materials such as polysaccharose, wax, lipophilic material of plant origin, hydrocarbons and any other suitable material or combination of materials. In some embodiments, additives, for example, hydrogel polymers, may be used to impart, e.g., mechanical strength, and/or to determine dissolving kinetics, for example, based on the extent of the hydrogel polymer cross linking, its concentration, its thickness, or the like. According to some embodiments, additives, such as, for example, those used in pharmaceutical preparations, may be included in the dissolvable material(s).

As device 10 travels through the body lumen, and comes in contact with, for example, body lumen fluids, one or more of gates 16 may begin to dissolve. In one embodiment, gate 16A, having the least volume, may dissolve first, thus gate 16A may "open" first and may allow fluid into inlet 14A first. Similarly, gate 16B may dissolve after gate 16A, and may therefore "open" after gate 16A; fluid may then flow into inlet 14B. Gate 16C may dissolve after gate 16B, and thus may "open" to allow fluid into inlet 14C. Other properties of the gates 16 and/or gate materials may determine the rate, speed, sequence and/or timing of the gates 16 opening.

Other suitable mechanisms may be used, for example, such that one or more of gates 16 dissolves or becomes substantially completely dissolved, after another gate 16 dissolves or becomes substantially completely dissolved.

Figure 4:
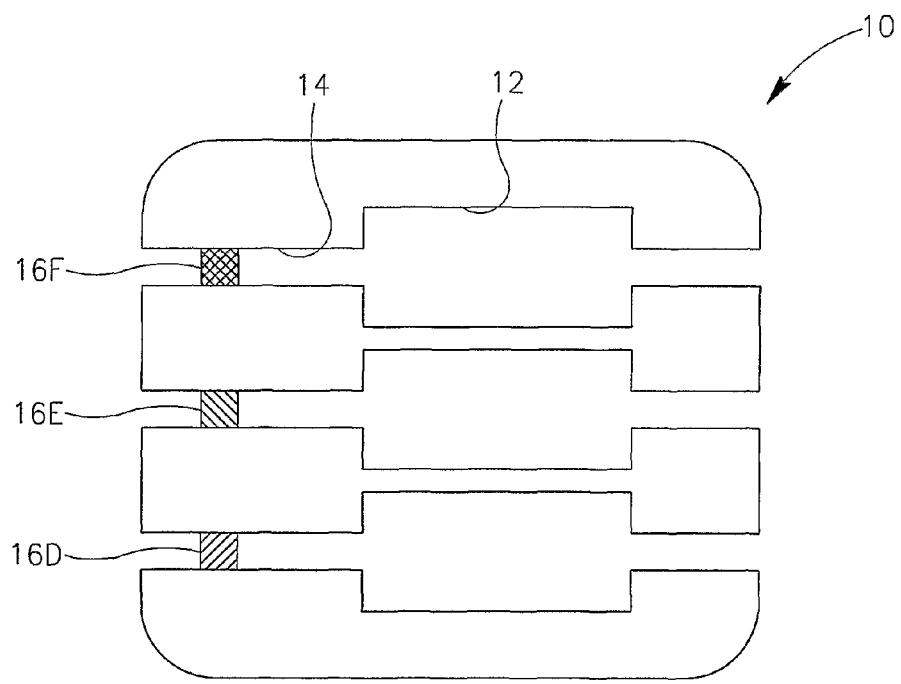

Reference is now made to FIG. 4, which illustrates another embodiment of device 10 having multiple gates 16. In this embodiment, gates 16D, 16E and 16F may be made of, for example, a pH sensitive material. Gate 16D may be sensitive to a pH of 4-6, for example, whereas gate 16E may be sensitive to a pH of 6-7, for example, and gate 16F may be sensitive to a pH of 7-8. Other suitable values or ranges may be used. According to some embodiments, the different gates 16 may dissolve with different kinetics at different pH levels.

Different bodily fluids may maintain different pH levels throughout the body. For example, the gastric fluids produced in the stomach may have a pH of less than 4; in the duodenum, the prevailing pH may be about 5.8 (or, for example, between 4 to 6); in the small intestine the pH may be about 5-7; and in the cecum the pH may be about 7-8. Therefore, as device 10 travels through the body lumen, gates 16D-16F may open at different areas in the GI tract, in accordance, for example, to the pH prevailing in each area.

According to some embodiments, differential pH in different parts of the GI tract may be used as a parameter for triggering, e.g., triggering of sampling or opening/closing of one or more gates 16. For example, a pH sensitive gating mechanism may control a sampling step, or may activate or initiate a sampling operation. According to one embodiment, a first gate 16 may enable sampling at a pH lower than 4, thus for example localizing the sampling to the stomach; a second gate 16 may enable sampling at a pH between approximately 5 and 7, thus for example localizing the sampling to the duodenum. Other parameters for triggering, other values or ranges, and other locations may be used. According to other embodiments, pattern or color recognition may be used as a parameter for triggering. For example, detection of green portions in GI tract in-vivo images obtained by an autonomous in-vivo imaging capsule or device, may indicate bile and locate the capsule at the bile duct area.

According to some embodiments, the gating materials may be sensitive to other parameters, such as, for example, temperature, pressure, enzymatic activity, specific bacteria, specific chemicals, specific materials, and so on.

According to one embodiment, triggering may be, for example, time dependant, dependant on environmental (typically endo-luminal) conditions, externally controlled, or dependant on a combination of parameters or conditions. For example, a swallowable device such as a capsule which is capable of imaging and/or sampling the GI tract as it is moved through the tract by peristalsis, may advance at a typically known rate, thus enabling the correlation of a time lapsed between swallowing or inserting of the capsule and a location of the capsule in the GI tract. Thus, according to one embodiment, a swallowable capsule may be programmed to sample, for example, approximately ten minutes after being swallowed or inserted, at which time the capsule is typically in the stomach; or, for example, approximately two hours after being swallowed or inserted, at which time the capsule is typically in the small intestine. Other time periods and locations may be used.

Due to natural differences between patients, a triggering parameter, such as time elapsed from swallowing or insertion, may be combined with one or more other triggering parameter(s), such as, for example, prevailing pH, temperature, pressure, ambient light, image data, or other suitable parameters, e.g., to ensure that the triggering occurs at a certain location. Mechanisms of triggering in-vivo devices are described, for example, in International Patent Application Number PCT/IL03/01080, filed on Dec. 16, 2003, published on Jul. 1, 2004 as WO 2004/054430, which is incorporated herein by reference in its entirety.

Once triggered, a certain event or function may take place or may be performed; for example, a sample or data may be collected into the in-vivo device 10. Known methods for collecting data (such as image data, pH information, temperature, electrical impedance, pressure, or the like) may be used, or other suitable methods may be used in accordance with embodiments of the present invention.

Figure 5:
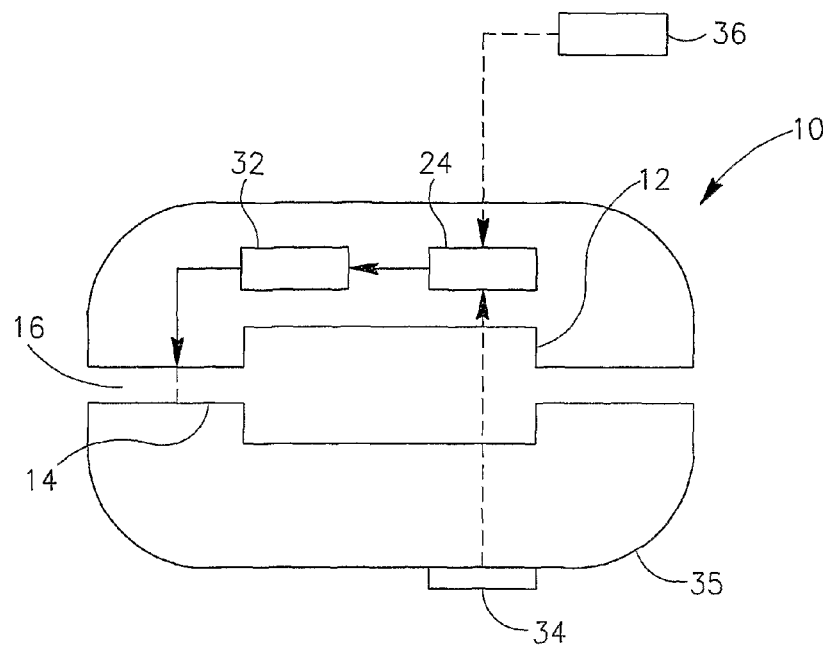

The embodiments described above relate to typically passive gating. Reference is now made to FIG. 5, which depicts a typically active gating mechanism in accordance with an embodiment of the invention. In this embodiment, gate 16 may be controlled by a controller 32. Device 10 may include a sensor 34, which may, according to one embodiment, be mounted on the outside of device 10. Other external or internal mounting locations may be used. Further included in device 10 may be a transceiver 24, e.g., able to communicate with an external processing unit 36.

Sensor 34 may sense for one or more body or body lumen parameters, such as, for example, pH, pressure, temperature, bacteria, or enzyme. When sensor 34 senses a desired (e.g., pre-defined) value or level of the sensed parameter (e.g., pH, pressure, temperature, bacteria, or enzyme), sensor 34 may send a first signal to transceiver 24. Transceiver 24 may then send a second signal to external processing unit 36, indicating that a desired location (e.g., based on specific pre-determined pH, pressure, temperature, bacteria, or enzyme) has been located. External processing unit 36 may then send a third signal to transceiver 24, which, in turn, may signal controller 32 to open gate 16. Transceiver 24 may communicate, for example, using RF, and/or may use other suitable transmitting and/or receiving methods, e.g., Infra Red (IR), microwave, or the like. Controller 32 may control the opening and/or closing of gates 16, for example, mechanically, electrically, magnetically or by any other suitable mechanism as known in the art. Gates 16 may optionally include, according to some embodiments, a switch, a solenoid, or other suitable mechanical gating elements. A spring or other similar structure or mechanism may be used; for example, a latch may allow a spring-operated gate to open and/or close.

According to some embodiments, controller 32 may control gates 16 directly based on a measured or sensed parameter. For example, if a measured parameter is above or below a predetermined value, controller 32 may operate automatically to open and/or close gates 16. Controller 32, which may be implemented using an ASIC or other suitable component, may include processing means for determining and/or controlling.

According to some embodiments, sensor 34 may include, for example, a pH sensor, a temperature sensor, a pressure sensor, a sensor of electrical impedance, an ultrasound detector, a radiation detector, etc.

According to some embodiments, sensor 34 may include an image sensor that may indicate a specific location in a body lumen based on, for example, color detection, color analysis, calorimetric analysis, light or wavelengths analysis, spectral analysis, image analysis, pattern recognition, or the like. In some embodiments, the image sensor may be complemented by illumination sources and an optical system, for example, as described above.

According to some embodiments, sensor 34 may include a light detector that can detect, for example, a difference in ambient light. A difference in ambient light may indicate, for example, that device 10 is exiting or entering a typically restricted tube (e.g., the esophagus or small intestine) or a typically more voluminous lumen (e.g., the stomach or large intestine). For example, in a restricted tube the light illuminated by an illumination unit and reflected from lumen walls to a light detector may be relatively lower or weaker than in a more voluminous lumen.

According to some embodiments, controller 32 may open or close gates 16 on a time dependant basis, e.g., when a pre-defined period of time elapses, or based on other time-related or timing criteria.

According to some embodiments, an external operator (e.g., a physician or a patient) may send through transceiver 24 to controller 32 a signal indicating a command, e.g., to close and/or open one or more of gates 16; and controller 32 may execute the received command.

Once gate 16 has opened, fluid may enter, or may be drawn into, sampling chamber 12 in one or more ways, for example, as described herein with reference to FIGS. 6, 7, 8 and 9.

Figure 6:
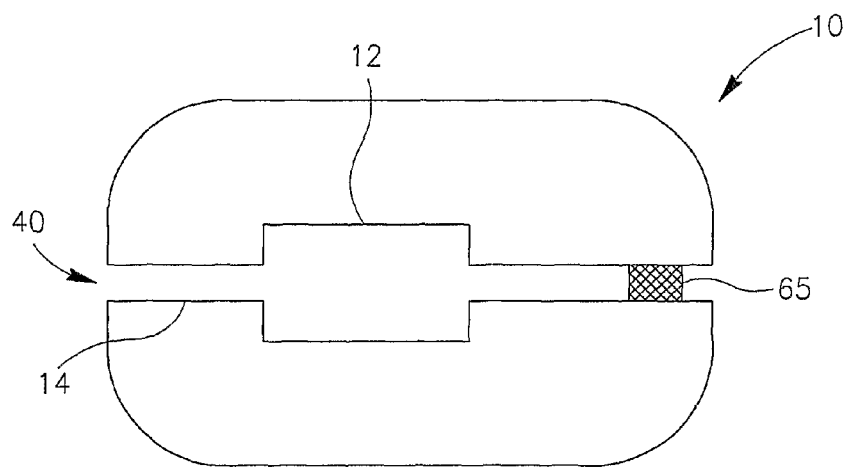
FIGS. 6 and 7 are schematic illustrations of a mechanism for drawing in fluid through capillary action according to embodiments of the invention.
Figure 7:
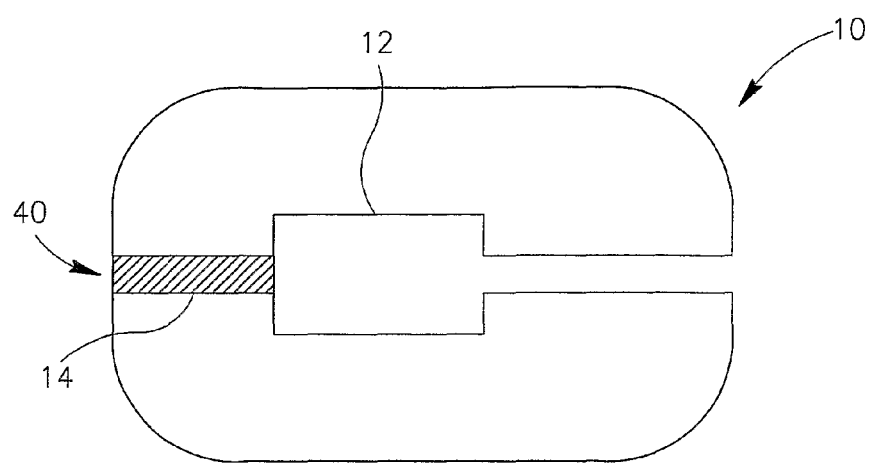

Reference is now made to FIGS. 6 and 7, which depict how a fluid may flow through sampling chamber 12, in accordance with embodiments of the present invention. FIG. 7 shows device 10 after testing sample 40 has entered inlet 14. Inlet 14 may be, for example, a capillary. Due to the function of capillaries, fluid may be drawn into sampling chamber 12. According to some embodiments, sampling chamber 12 may be, but need not be, of larger dimensions than inlet 14.

According to one embodiment, the in-vivo device may be constructed and/or may operative similarly to embodiments of the in-vivo device described in U.S. patent application Ser. No. 10/046,540, entitled "A System and Method for Determining In-vivo Body Lumen Conditions", filed on Jan. 16, 2002, published on Aug. 15, 2002 as United States Patent Application Publication Number 2002/0111544, which is hereby incorporated by reference in its entirety.

According to some embodiments, capillary action may sample endo-luminal fluids, for example, at a rate of a few micro-liters per minute. Other rates may be used. Due to the restricted size of the capillary (e.g., inlet 14), relatively small volumes of fluids may be sampled, thereby allowing, for example, substantially continuous sampling for typically short periods of time (e.g., less than one hour).

According to an embodiment of the invention, as shown in FIG. 6, an extended sampling period may be obtained by using a fluid absorbent component 65, which may include a sponge or any other suitable absorbent, typically porous material or matrix. Absorbent component 65 may be placed, for example, at the end or near the end opposite inlet 14. Absorbent component 65 may serve as a drain for samples 40, thus functioning as a pump to draw in a fluid sample 40 that has entered inlet 14 (e.g., initially due to capillary forces). Due to the larger capacity of absorbent component 65 (e.g., 0.5-2 milliliters), a relatively large volume of fluids may be sampled, thereby enabling sampling over a longer period of time.

Figure 8:
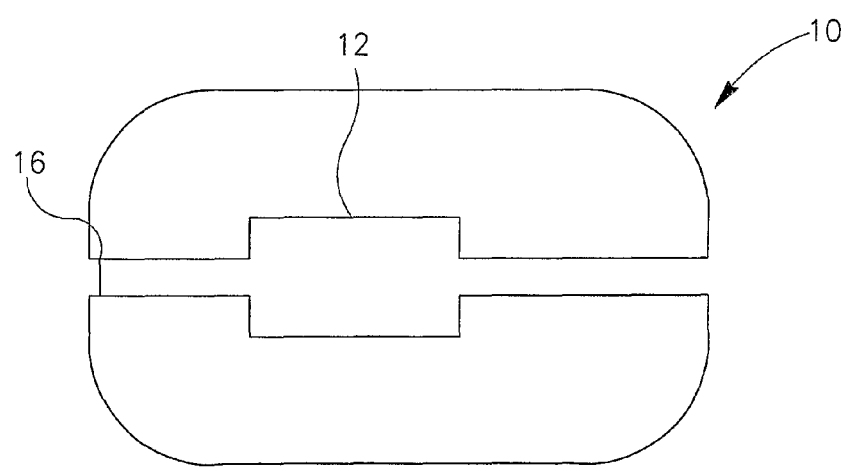
FIG. 8 is a schematic illustration of a mechanism for drawing in fluid through a vacuum chamber, according to an embodiment of the invention.

Reference is now made to FIG. 8, which depicts yet another embodiment of the present invention. Sampling chamber 12 may be vacuumized, for example, before device 10 is swallowed; and sampling chamber 12 may thus include a vacuum sealed by gate 16. As soon as gate 16 is opened, the vacuum pressure from chamber 12 may draw in a testing sample from the surrounding fluid.

Figure 9:
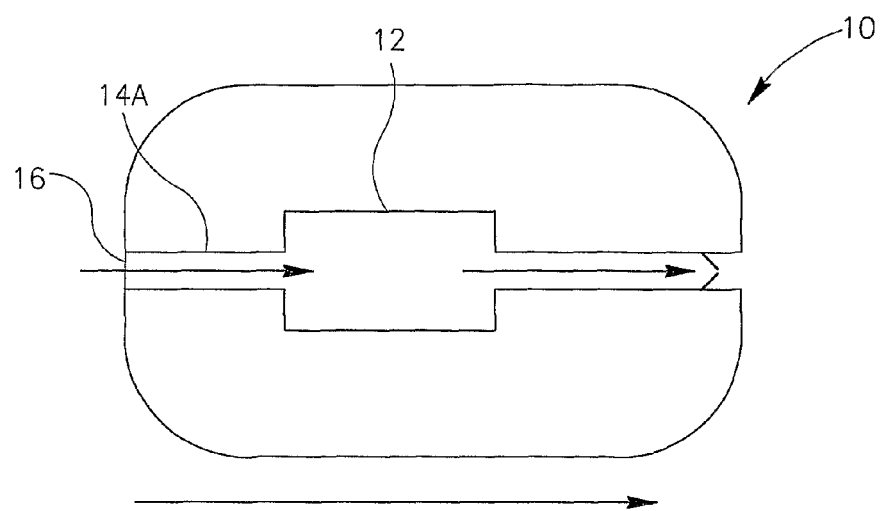
FIG. 9 is a schematic illustration of a flow-through mechanism according to an embodiment of the invention.

In another embodiment of the present invention, as shown in FIG. 9, inlet 14 may be particularly wide, e.g., to enable fluid to pass through inlet 14 freely. After gate 16 has opened, the fluid that surrounds device 10, for example, endo-luminal fluid, may flow freely through inlet 14A, which may be especially wide to allow for fluid to flow through it in accordance with the motions of, for example, peristalsis and normal intestinal movement.

Figure 10:
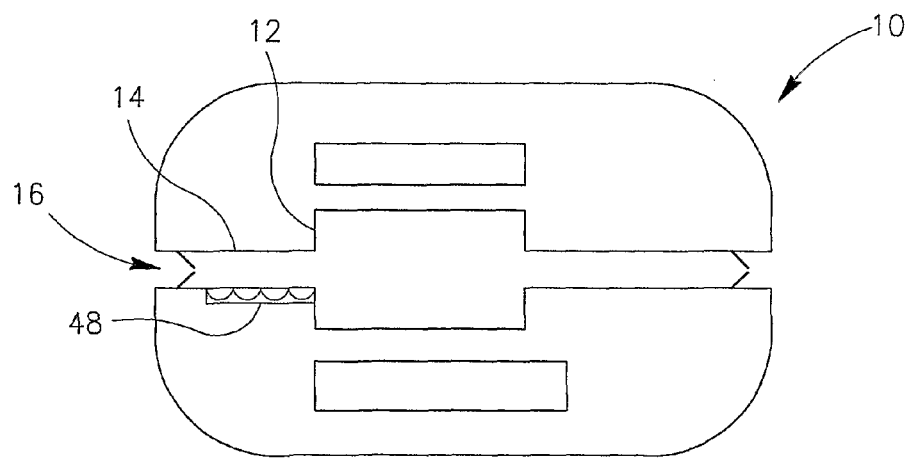
FIG. 10 is a schematic illustration of a pumping mechanism according to an embodiment of the invention.

In yet another embodiment of the present invention, as shown, for example, in FIG. 10, fluid may be passed into a sampling chamber, or a drug stored in chamber 12 can be released, through the use of a pumping mechanism 48. The pumping mechanism 48 may have one or more pumps, and/or may perform one or more functions. For example, as long as pumping mechanism 48 is not activated, it may function as a closed gate. Once pumping mechanism 48 is triggered, for example, through one of the gating mechanisms described above or herein, pumping mechanism 48 may pump out a drug, and/or may pump in a testing sample through inlet 14 into sampling chamber 12. Pumping mechanism 48 may include, for example, a suitable micro-pump apparatus.

Figure 11:
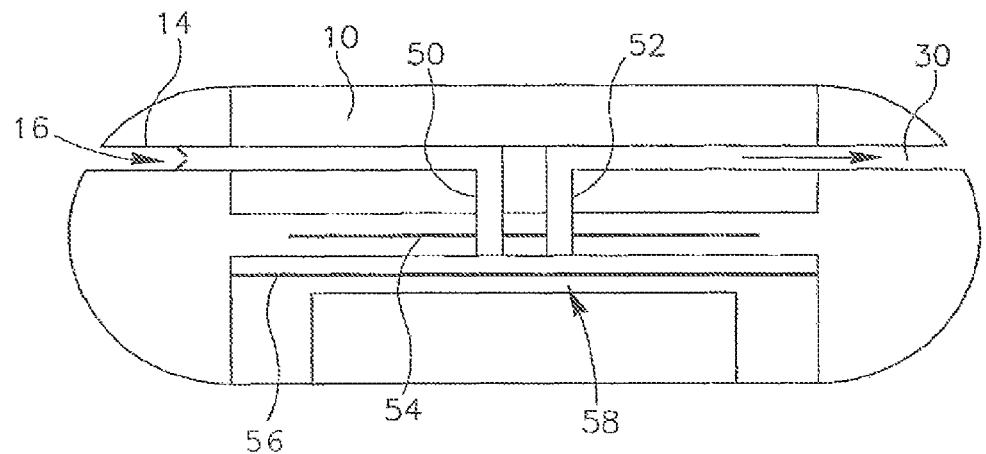
FIG. 11 is a schematic illustration of a flowing mechanism according to an embodiment of the invention.

Reference is now made to FIG. 11, which illustrates an embodiment of the present invention in which a fluid may be moved in and out of an in-vivo device. The device 10 may include, for example, inlet 14, gate 16, outlet 30, an individual well inlet 50, an individual well outlet 52, an upper flexible conductive plate 54, and a lower flexible conductive plate 56. Each flexible conductive plate 54 and 56 may be surrounded by a flexible membrane 58. Membrane 58 may be, for example, a thin non-conductive membrane.

Flexible conductive plates 54 and 56, as well as flexible membrane 58, may operate in a manner similar to capacitor plates and membranes. A current may be provided to, or made to go through, the conductive plates 54 and/or 56, thereby building up or creating a voltage on the conductive plates. According to some embodiments, for example, conductive plates 54 and/or 56 may be connected to the device 10 power source (e.g., power source 26 of FIG. 2) in a suitable way to allow a voltage to build up on the conductive plates 54 and 56. Other suitable methods for building a voltage on plates 54 and/or 56 may be used.

The voltages on flexible conductive plates 54 and 56 may be sequenced, for example, in a manner similar to the sequencing used in CCD technology, where it is used to shift charges sequentially. Such sequencing is described for example, in the article by Theuwissen A. J. P., Philips J. of Research Vol. 48 No. 3 1994, pp. 147-158, which is hereby incorporated by reference.

Figure 12:
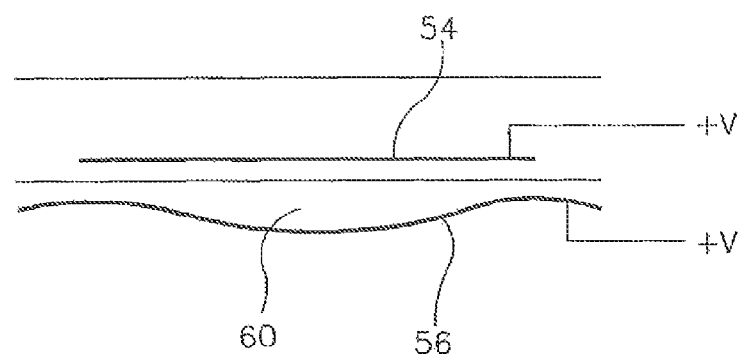
FIG. 12 is a schematic illustration of a pumping mechanism according to another embodiment of the invention.

In some embodiments, when the voltages on both flexible conductive plates 54 and 56 are roughly equal, conductive plates 54 and 56 may push away from each other, as shown, for example, in FIG. 12. Because conductive plates 54 and 56 are repelled from each other, the space between conductive plates 54 and 56 may form an opening, or a well 60. Opposing voltages on conductive plates 54 and 56 may keep well 60 closed.

According to one embodiment, the device 10 need not include gate 16; for example, the opening and closing of well 60 (e.g., due to movement of conductive plates 54 and/or 56) may serve to gate the sampling, or expelling of a substance from well 60.

In an embodiment of the present invention, there may be multiple testing wells within a sampling chamber. Testing sample fluid may move between the multiple wells, or through the sampling chamber and out of the capsule.

Figure 13:
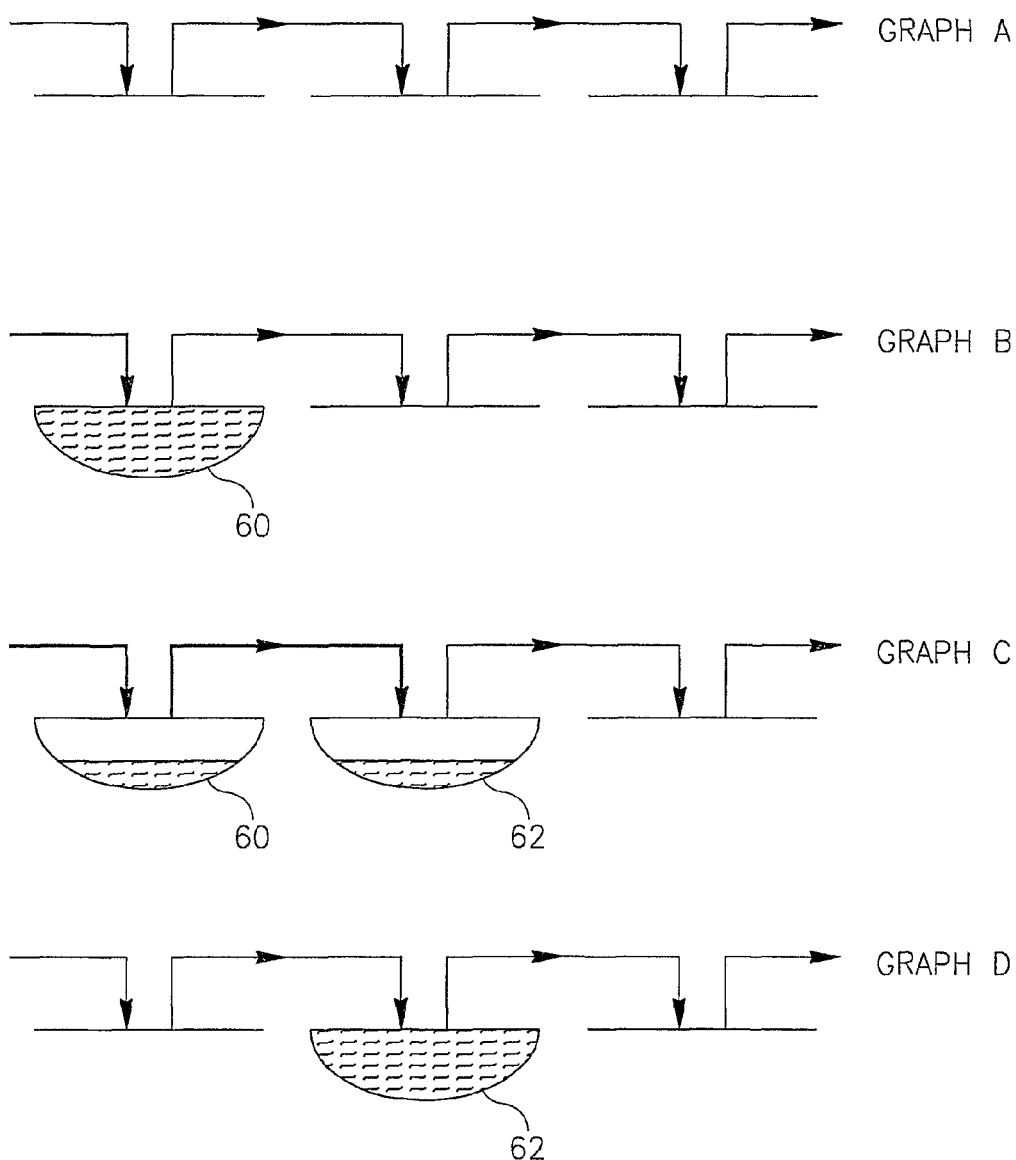
FIG. 13 is a schematic illustration of a pumping mechanism according to yet another embodiment of the invention.

Reference is now made to FIG. 13, which illustrates the operation of a pump used to shift fluid between multiple wells, in accordance with an embodiment of the invention. In graph A, no wells are formed. In graph B, a well 60 may be formed, since in the first sampling chamber the voltages of flexible conductive plates 54 and 56 (of FIGS. 11 and 12) are generally equal. In graph C, the voltages on flexible conductive plates 54 and 56 in well 60 may begin to become unequal, such that well 60 may begin to close. This may, for example, cause fluid from well 60 to move into a well 62 which may be opening since the voltages on plates 54 and 56 in well 62 may be becoming more equal. Thus, the fluid may shift from well 60 to well 62, e.g., as shown in graph D.

According to embodiments of the invention, sampling chambers and/or wells my include reagents or indicators that may be configured to react with a sample or with components of a sample to give indication of, for example, substances or a concentration of substances within the sample. Such reagents or indicators may include, for example, proteins or other biologically active molecules, color indicators, ions or larger charged molecules, or the like. A reaction occurring in a sampling chamber or well may cause changes in the well, such as an optical or electrical change; an indication of the change, or data representing properties of the change, may be transmitted externally from the body, for example, by imaging the wells, and may be detected by an external operator. An imager within the in-vivo device may partially or completely include a sampling chamber or well, and may image the chamber, and such images may be transmitted from the device to an external receiver/recorder.

Some embodiments of the invention may include a method for in-vivo sampling, which may include, for example: collecting a substance in a sampling chamber of an in-vivo device, wherein the sampling chamber has an opening closeable by a gate; acquiring (e.g., in-vivo) an image of the sampling chamber; opening the gate at a point in time after insertion of the in-vivo device into a body; and/or other suitable operations.

Figure 14:
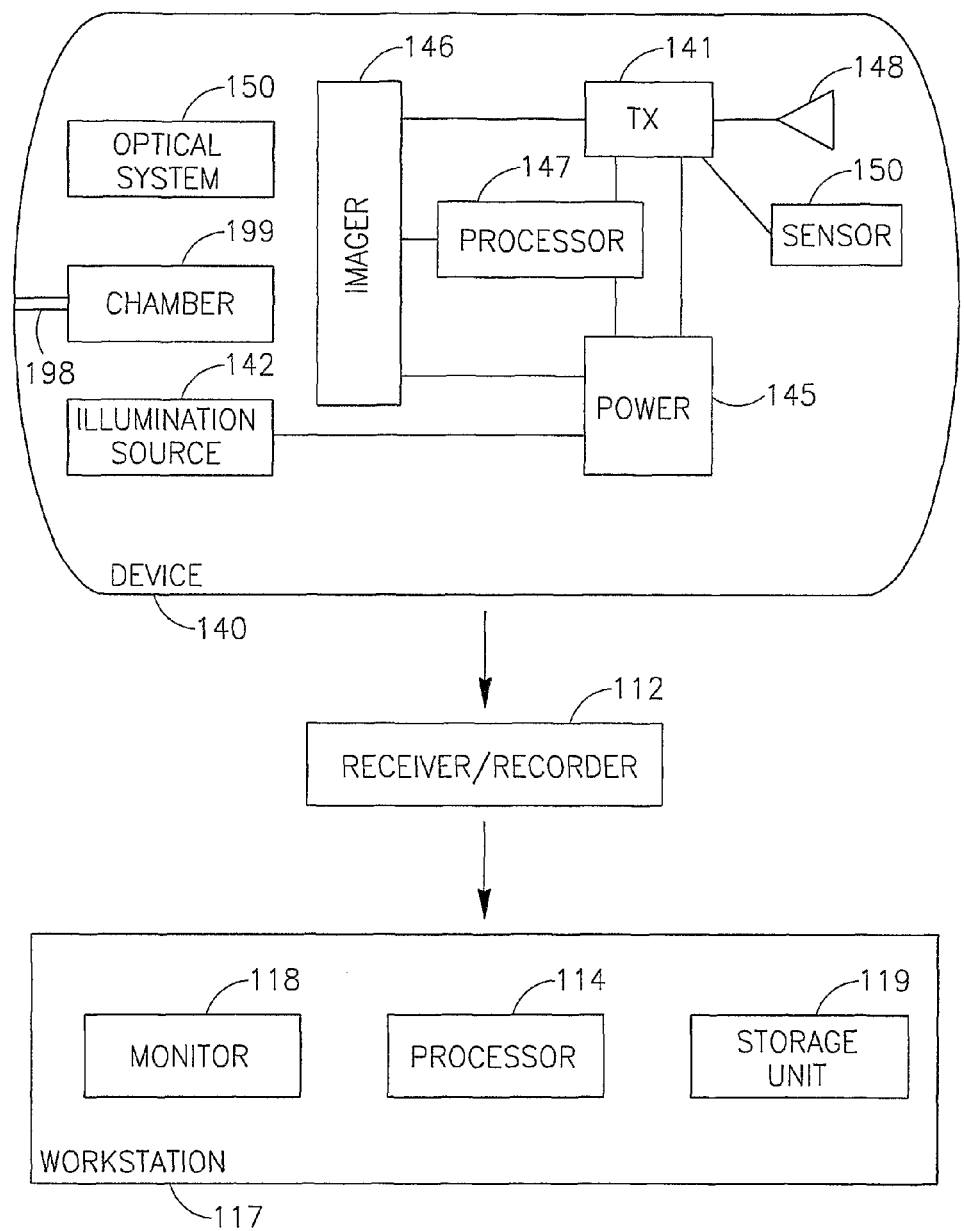
FIG. 14 is a schematic illustration of an in-vivo system according to an embodiment of the invention.

FIG. 14 shows a schematic illustration of an in-vivo imaging system in accordance with some embodiments of the present invention. One or more components of the system may be used in conjunction with, may be operatively associated with, or may be included in, the device 10 of FIGS. 1-11, components and elements shown in any of FIGS. 1-13, components and elements described with reference to any of FIGS. 1-13, or other in-vivo devices in accordance with embodiments of the invention.

In one embodiment, the system may include a device 140 having an imager 146, one or more illumination sources 142, a power source 145, and a transmitter 141. In some embodiments, device 140 may be implemented using a swallowable capsule, but other sorts of devices or suitable implementations may be used. Outside a patient's body may be, for example, an external receiver/recorder 112 (including, or operatively associated with, for example, an antenna or an antenna array), a storage unit 119, a processor 114, and a monitor 118. In one embodiment, for example, processor 114, storage unit 119 and/or monitor 118 may be implemented as a workstation 117, e.g., a computer or a computing platform.

Transmitter 141 may operate using radio waves; but in some embodiments, such as those where device 140 is or is included within an endoscope, transmitter 141 may transmit/receive data via, for example, wire, optical fiber and/or other suitable methods. Other known wireless methods of transmission may be used. Transmitter 141 may include, for example, a transmitter module or sub-unit and a receiver module or sub-unit, or an integrated transceiver or transmitter-receiver.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit information. In one embodiment, device 140 may be autonomous and non-remote-controllable; in another embodiment, device 140 may be partially or entirely remote-controllable.

In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

In one embodiment, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In one embodiment, imager 146 in device 140 may be operationally connected to transmitter 141. Transmitter 141 may transmit images to, for example, external transceiver or receiver/recorder 112 (e.g., through one or more antennas), which may send the data to processor 114 and/or to storage unit 119. Transmitter 141 may also include control capability, although control capability may be included in a separate component, e.g., processor 147. Transmitter 141 may include any suitable transmitter able to transmit image data, other sensed data, and/or other data (e.g., control data) to a receiving device. Transmitter 141 may also be capable of receiving signals/commands, for example from an external transceiver. For example, in one embodiment, transmitter 141 may include an ultra low power Radio Frequency (RF) high bandwidth transmitter, possibly provided in Chip Scale Package (CSP).

In some embodiments, transmitter 141 may transmit/receive via antenna 148. Transmitter 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transmitter 141 may include a receiver which may receive signals (e.g., from outside the patient's body), for example, through antenna 148 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

Optionally, in one embodiment, transmitter 141 may include a processing unit or processor or controller, for example, to process signals and/or data generated by imager 146. In another embodiment, the processing unit may be implemented using a separate component within device 140, e.g., controller or processor 147, or may be implemented as an integral part of imager 146, transmitter 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In one embodiment, for example, the processing unit or controller may be embedded in or integrated with transmitter 141, and may be implemented, for example, using an ASIC.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optional optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminated light, and/or performing other light processing operations.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In one embodiment, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In one embodiment, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to external receiver/recorder 112. Other constant and/or variable capture rates and/or transmission rates may be used.

Optionally, device 140 may include one or more sensors 143, instead of or in addition to a sensor such as imager 146. Sensor 143 may, for example, sense, detect, determine and/or measure one or more values of properties or characteristics of the surrounding of device 140. For example, sensor 143 may include a pH sensor, a temperature sensor, an electrical conductivity sensor, a pressure sensor, or any other known suitable in-vivo sensor.

Device 140 may further include one or more components or mechanisms of the device 10 of FIGS. 1-11, and/or of other in-vivo devices in accordance with embodiments of the invention, for example, one or more sampling chambers 199, one or more gates 198, chambers, wells, inlets, tubes, pipes, capillaries, plugs, dissolvable materials, dissolvable gates, dissolvable plugs, containers, markers, indicators, reagents, absorbent materials, controllers, pumps, or the like.

In some embodiments, known in-vivo sampling methods may be used to collect fluid or tissue samples. According to an embodiment of the invention, an indicator may be included in the in-vivo device so as to enable an analysis or detection on board the in-vivo device. For example, a sampling chamber on board a swallowable capsule may include a tumor marker specific reactant, which may react with a tumor marker possibly contained in a collected sample. A reaction occurring within a sampling chamber may result in an indication (e.g., a change in electric charge, a change of color or other optical parameters, or the like) of the presence of a tumor marker. For example, a system of monoclonal antibodies directed against different antigenic determinants on CA19-9 may be used. Other antibodies or antigens may be used, for example, anti-TNF-alpha monoclonal antibodies may be used in the detection of Crohn's disease. Raw data, or analyzed data based on such reactions or detections, may be transmitted, e.g., by the in-vivo device to an external receiver/recorder or system.

In some embodiments, a sensor which may be included in the in-vivo device may sense a reaction in a sampling chamber and a signal may be sent, typically through a wireless transmitter to an external receiving unit.

According to some embodiments, a patient may be pretreated or treated, e.g., before insertion or swallowing of the in-vivo device, or after such insertion or swallowing and before sampling. For example, a marker containing composition (e.g., a radio-labeled marker) may be administered to a patient prior to the in-vivo sampling step, and the sampling step may then include, for example, a radioactive detection step. According to other embodiments, a patient may be pretreated in order to induce, enhance or inhibit certain bodily functions prior to the in-vivo sampling test.

According to one embodiment, the pre treating step may include, for example, administering to a patient an agent causing stomach contractions. According to another embodiment, the pre treating step may include administering a composition which may elevate the acidity of the stomach and/or raise the pH in the pancreas, to obtain, for example, secretion of pancreatic juices into the GI tract. Administering a composition according to embodiments of the invention may include a high protein drink or an injection of secretin, a 27 amino acid basic peptide which may be a potent stimulus for bicarbonate secretion. Other suitable compositions having other active agents may be administered to a patient in any suitable way.

According to an embodiment of the invention, the pre treating step may be coordinated with the sampling step. For example, in order to obtain a sample having a high concentration of pancreatic juices, a pre treating step which may cause secretion of pancreatic juices to the duodenum may be timed such that a sampling capsule will be triggered for sampling in the duodenum within the window (e.g., time window and location) of pancreatic secretion.

According to some embodiments, a system operable in accordance with embodiments of the invention may be an in-vivo sampling device that is moved through a body lumen. According to one embodiment, the device is moved through the GI tract. At a specific location the device may be activated. The location may be, for example, a drainage area for secretions from a duct, such as a bile duct. Thus, sampling bile or other secretions (e.g., pancreatic secretions) may be enabled according to embodiments of the invention.

According to embodiments of the invention, the in-vivo device may include a sensor, such as an image sensor or a pH sensor which may collect in-vivo data. The collected in-vivo data (e.g., images or pH values) may be processed on board the in-vivo device, for example, to automatically activate the in-vivo device (or a component or function thereof) according to the collected data. The in-vivo device may include other suitable components, such as light source(s), a processor, transmitter, optical system, power source or power receiving element, etc.

According to other embodiments, collected or sensed data may be transmitted from the in-vivo device to an external receiver unit. Processing and activation of the device may be performed by the receiver unit, and a command from the external receiver unit or from another external source, may be sent to the in-vivo device to activate the in-vivo device (or a component of function thereof). The command may be, for example, an electrical signal transmitted wirelessly to the in-vivo device. According to one embodiment, the in-vivo device may include a receiver to receive an external signal, and to operate the device (or a component of function thereof) according to the signal or in response to the signal. According to some embodiments of the invention, activation of the in-vivo device (or a component of function thereof) may be passive, e.g., not in response to an external command or external signal.

In some embodiments, a sample may be analyzed on board the in-vivo device (for example, as described above or herein), and an indication of the analysis may be transmitted. According to other embodiments, raw data may be transmitted from the in-vivo device to an external receiving and analyzing unit.

Various aspects of the various embodiments disclosed herein are combinable with the other embodiments disclosed herein.

Although portions of the discussion herein may relate to sampling, collection and/or release of fluid or body lumen fluid, the present invention is not limited in this regard, and may include, for example, sampling, collection and/or release of one or more materials, substances, fluids, solids, gases, materials including both lumen fluids and/or solids, or the like.

Device 10, device 140, and/or other devices described herein typically may be, or may include, an autonomous swallowable capsule, but such devices may have other shapes and need not be swallowable and/or autonomous. Embodiments of the invention are typically autonomous, and are typically self-contained. For example, a device may be a capsule or other unit where all the components are substantially contained within a container or shell, and where device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

Although portions of the discussion herein may relate to a chamber which may be or include, for example, a container, a cavity, a well, a compartment, or the like, embodiments of the invention are not limited in this regard. For example, in some embodiments, a chamber may be or may include, for example, a chromatography unit, a chromatography strip, a chromatography component, a testing unit, a testing strip, a paper-like strip or unit, a plate, a plate-like strip or unit, a testing component, or the like. In some embodiments, for example, a chamber need not have properties of a container or a cavity, or may be implemented as a testing component or unit.

A device, system and method in accordance with some embodiments of the invention may be used, for example, in conjunction with a device which may be inserted into a human body. However, the scope of the present invention is not limited in this regard. For example, some embodiments of the invention may be used in conjunction with a device which may be inserted into a non-human body or an animal body.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

What is claimed is:

1. An in-vivo device comprising:
   a sampling chamber able to store a sample of a body lumen substance;
   a first opening to allow said body lumen substance to enter said chamber from the body lumen;
   a gate able to close and open said first opening of said sampling chamber;
   a second opening to allow said body lumen substance to exit said chamber to the body lumen;
   a first, flexible conductive plate able to repel from or attract to a second conductive plate when substantially equal or opposing current, respectively, is supplied to said first and second conductive plates, wherein said first and second conductive plates are located within said sampling chamber;

a power source to supply said current to said first and second conductive plates;

a first well formed when said first and second conductive plates are repelled from each other, said first well comprising a first reagent; and a second well formed when said first and second conductive plates are repelled from each other, said second well comprising a second reagent, wherein said sample is able to advance from said first well to said second well when said supplied current becomes opposing current in said first well while in said second well the current becomes substantially equal;

wherein said in-vivo device is a swallowable capsule.

2. The in-vivo device of claim 1, wherein said gate comprises a dissolvable material.

3. The in-vivo device of claim 1, comprising an imager to acquire an image of said body lumen substance stored in said chamber.

4. The in-vivo device of claim 1, wherein said in-vivo device is autonomous.

5. The in-vivo device of claim 1, wherein the first conductive plate is opposing the second conductive plate.

6. The in-vivo device of claim 1, wherein said gate is a passive gate.

7. The in-vivo device of claim 1, wherein said gate is an active gate.

8. The in-vivo device of claim 7, comprising:

a controller able to open said gate when a pre-defined condition is met.

9. The in-vivo device of claim 7, comprising:

a controller able to open said gate in response to a signal.

10. The in-vivo device of claim 9, wherein said signal is received from an external transmitter.

11. The in-vivo device of claim 9, wherein said signal is generated based on an analysis of an in-vivo image.

12. The in-vivo device of claim 9, wherein said signal is generated by an in-vivo sensor in response to a sensed parameter.

13. The in-vivo device of claim 12 wherein said sensed parameter is a parameter selected from a group consisting of: temperature, pH, pressure, bacteria, and enzyme activity.

14. The in-vivo device of claim 1, comprising an absorbent component to absorb at least a portion of said body lumen substance.

15. The in-vivo device of claim 1, wherein said chamber comprises a vacuum.

16. The in-vivo device of claim 1, comprising a capillary to transport said body lumen substance into said chamber.

17. The in-vivo device of claim 1, wherein said first opening comprises a wide inlet to freely transport said body lumen substance into said chamber.

18. The in-vivo device of claim 1, comprising a pump to pump in said body lumen substance into said chamber.

19. The in-vivo device of claim 1, comprising a pump to pump out a content from said chamber.

20. The in-vivo device of claim 1, wherein said chamber comprises an indicator to interact with said body lumen substance.

21. A method comprising:

collecting a substance in a first chamber of an in-vivo device, wherein the in-vivo device is a swallowable capsule and comprises (a) a gate able to close and open a first opening of said first chamber, (b) a first, flexible conductive plate able to repel from or attract to a second conductive plate when substantially equal or opposing current, respectively, is supplied to said first and second conductive plates, (c) a first well formed when said first and second conductive plates are repelled from each other, and (d) a second well formed when said first and second conductive plates are repelled from each other;

said first well comprising a first reagent, said substance entering said first well through a first opening in said chamber;

allowing said substance to advance from said first well to a second well of the in-vivo device, said second well comprising a second reagent; and allowing said substance to exit the in-vivo device through a second opening in said chamber.

22. The method of claim 21, comprising acquiring in-vivo an image of said sampling chambers.

23. The method of claim 21, wherein the openings open in response to a sensed parameter, wherein said parameter is selected from the group consisting of: temperature, pH, pressure, bacteria, and enzyme activity.

* * * * *